(12) United States Patent
Weinstein et al.

(10) Patent No.: US 6,187,291 B1
(45) Date of Patent: *Feb. 13, 2001

(54) METHOD AND DEVICE FOR FACILITATING COMBINED AEROSOL AND ORAL TREATMENTS FOR DIABETES MELLITUS

(76) Inventors: Robert Weinstein, 177 Commonwealth Ave., Boston, MA (US) 02116; Allan Weinstein, 9205 Pegasus Ct., Potomac, MD (US) 20854

( * ) Notice: Under 35 U.S.C. 154(b), the term of this patent shall be extended for 0 days.

This patent is subject to a terminal disclaimer.

(21) Appl. No.: 09/392,515

(22) Filed: Sep. 9, 1999

Related U.S. Application Data

(60) Provisional application No. 60/102,076, filed on Sep. 28, 1998.

(51) Int. Cl.⁷ .............................. A61K 9/12; A61K 9/00
(52) U.S. Cl. ......................... 424/45; 424/400; 424/451; 424/464; 424/489; 514/866
(58) Field of Search ................... 206/538, 570; 424/400

(56) References Cited

U.S. PATENT DOCUMENTS

| | | | |
|---|---|---|---|
| 3,638,603 | * 2/1972 | Conover | 116/121 |
| 3,981,398 | * 9/1976 | Boshoff | 206/223 |
| 4,039,080 | 8/1977 | Capuccilli . | |
| 4,250,998 | * 2/1981 | Taylor | 206/570 |
| 4,593,819 | 6/1986 | Will . | |
| 4,736,849 | 4/1988 | Leonard et al. . | |
| 4,848,587 | * 7/1989 | Nipp | 206/571 |
| 5,181,189 | 1/1993 | Hafner . | |
| 5,377,841 | 1/1995 | Varon . | |
| 5,390,791 | * 2/1995 | Yeager | 206/438 |
| 5,830,490 | 11/1998 | Weinstein et al. . | |
| 5,941,241 | * 8/1999 | Weinstein et al. | 128/200.23 |

FOREIGN PATENT DOCUMENTS 830269  5/1938  (FR) .

OTHER PUBLICATIONS

Intrapulmonary administration of insulin to healthy volunteers, J.H. Jendle & B.E. Karlberg, Journal of Internal Medicine, 1996, vol. 240, pp. 93–97.

Effects of intrapulmonary insulin in patients with non–insulin–dependent diabetes, J.H. Jendle & B.E. Karlberg, Scand. J. Clin. Lab Invest, 1996, vol. 56, pp. 555–561.

Preliminary Study of the Efficacy of Insulin Aerosol Delivered by Oral Inhalation in Diabetic Patients, Beth L. Laube, et al., JAMA, Apr. 1993, vol. 269, No. 16, pp. 2106–2109.

The Lung As an Alternative Route of Delivery for Insulin in Controlling Postprandial Glucose Levels In Patients with Diabetes, Beth L. Laube et al., Chest, vol. 114, No. 6, Dec. 1998, pp. 1734–1739.

(List continued on next page.)

*Primary Examiner*—Thurman K. Page
*Assistant Examiner*—P. E. McQueeney
(74) *Attorney, Agent, or Firm*—Robert R. Deleault, Esq.; Mesmer & Deleault, PLLC

(57) ABSTRACT

A dispensing container which incorporates an aerosolizable topical insulin preparation, at least one oral hypoglycemic agent, and indicia and instructions for their coordinated use as a single therapeutic regimen for the treatment of diabetes mellitus in a human, and a method for treating diabetes mellitus which employs such a device.

15 Claims, 2 Drawing Sheets

OTHER PUBLICATIONS

Insulation Without Injections??? What Have You Been Puffing?, Robert I. Misbin, Chest, vol. 114, No. 6, Dec. 1998, p. 1513.

Novel Forms of Insulin Delivery, Christopher D. Saudek, Endocrinology and Metabolism Clinics of North America, vol. 26, No. 3, Sep. 1997, pp. 599–610.

Systems Analysis of Adverse Drug Events, Lucian L. Leape et al., JAMA, vol. 274, No. 1, Jul. 5, 1995, pp. 35–43.

Error In Medicine, Lucian L. Leape, JAMA, vol. 272, No. 23, Dec. 21, 1994, pp. 1851–1857.

Multiple Dose Regimens: Impact on Compliance, Donald P. Tashkin, Chest, vol. 107, No. 5, May 1995, Supplement, pp. 176S–182S.

Abstract of "Time–action profile of inhaled insulin," L. Heinemann et al., Diabet. Med., vol. 14, No. 1, Jan. 1997, pp. 63–72.

* cited by examiner

| Insulin Reservior | Nebulizing Device | Oral Hypoglycemic Medication |

Coordinate as follows: _____

Aerosolize as follows: _____

Fig. 2

METHOD AND DEVICE FOR FACILITATING COMBINED AEROSOL AND ORAL TREATMENTS FOR DIABETES MELLITUS

RELATED APPLICATIONS

The applicants wish to claim the benefit of U.S. Provisional Patent Application Ser. No. 60/102,076, dated Sep. 28, 1998, for COMBINED TREATMENT OF DIABETES MELLITUS WITH USE OF INHALATIONAL AND ORAL MEDICATIONS in the names of Robert Weinstein and Allan Weinstein.

BACKGROUND OF THE INVENTION

1. Field of the Invention

The present invention relates to method and device for organizing and coordinating combined aerosol and oral medications for treating diabetes mellitus.

2. Description of the Prior Art

Packaging has been developed for aiding the users of medications to comply with proper administration. Dispensing apparatus associated with multiple day administrative drugs are typically directed to the administration of pills or capsules, or similar solid medication.

U.S. Pat. No. 4,039,080, for example, discloses a tray having individual compartments for pills which may contain a week's medication with indicia indicating the day of the week and the time of the day the medication is to be taken.

U.S. Pat. No. 4,553,670 discloses another device comprising a support on which are located two different ingestible medical substances in a single dose form with an adjacent portion for instructional information.

U.S. Pat. No. 4,593,819 discloses a covered pill tray of rectangular configuration having an array of open-topped compartments to hold a supply of medication arranged by the day and time of taking the medication.

U.S. Pat. No. 4,736,849 discloses a method and another type of dispenser for the storage and dispensing of calendar-oriented pills. U.S. Pat. No. 5,181,189 discloses a device for storage and time-regulated dispensing of drugs which includes a drug container to which is secured a signal generator.

U.S. Pat. No. 5,377,841 discloses a sleep therapy package which includes an audio recording for inducing sleep.

U.S. Pat. No. 5,830,490 discloses an organizational tool for a lay person to organize oral medications together with topical medications, and a method for reducing medication error and enhancing therapeutic compliance of combined topical and systemic modality therapeutic regimens. This patent however, does not disclose the application of such devices and methods to the treatment of diabetes.

Diabetes mellitus is a chronic illness caused by an effective lack of insulin and manifested by elevation of blood sugar. It is the fourth leading cause of death by disease in the United States and the leading cause of irreversible blindness and chronic renal failure. Treatment for diabetes is directed to lowering blood sugar and to preventing long term complications which include neuropathy, accelerated atherosclerosis, myocardial infarction, gangrene of the lower extremities, retinopathy and nephropathy. Diabetic individuals are commonly required to assiduously comply with treatments over very long periods in order to avoid these complications. Measures to enhance convenience and compliance are therefore especially desirable.

The two pharmacologic modalities presently used to lower blood sugar are oral hypoglycemic (antidiabetic) agents and insulin. Insulin replacement is presently accomplished by injection and is based upon the lack of insulin or limitation of its action in diabetes mellitus. Oral antidiabetic agents are not chemically akin to insulin and their sugar-lowering mechanism differs from the action of direct insulin replacement. Oral hypoglycemic agents and insulin are presently therapeutically utilized alone or in concert with each other, according to the needs of the diabetic individual. Some individuals are best treated with more than one oral agent.

Oral hypoglycemic agents presently include: sulfonylureas, biguanides, alpha-glucosidase inhibitors and thiazolidinediones. Examples of sulfonureas are tolbutamide, acetohexamide, tolazamide, and chlorpropamide, so-called first-generation agents, and glyburide, glipizide, and glimeperide, second-generation agents. First and second generation sulfonureas differ in their potency, adverse effects and durations of action. Metformin is an example of a biguanide, acarabose is an example of a glucosidase inhibitor, and troglitizone is an example of a thiazolidinedione.

Recent clinical feasablity studies in diabetic individuals have disclosed that insulin can be administered topically to the nasal and lung mucosa and so be absorbed and function to reduce blood sugar. As with injected insulin, oral hypoglycemic medication may be utilized together with insulin administered by respiratory aerosol to lower blood sugar. Because of the more limited action of topical insulin compared to injected insulin, it is likely that topical insulin usage will frequently require complementary use of oral antidiabetic agents for diabetic control.

Compliance with medication therapy is important in successful long-term diabetic care. Health care experts estimate that half of the 1.8 billion prescription medications dispensed yearly are not taken as prescribed. Adherence to medication is known to be adversely affected by inconvenience, and complexity of use. Conversely, compliance and the risk of medication error is improved with measures to increase convenience, establish simplicity, and reduce confusion.

Topical aerosol medications are commonly used to treat respiratory disorders. Poor compliance, and frequent errors in their use is known to occur and result in relapse of respiratory symptoms such as cough, shortness of breath, wheezing, nasal congestion and chest congestion. The result of non-compliance with diabetes treatment may not produce such apparent and reversable consequences, but would rather dispose the individual to long-term, insidious and irreversible damage.

Multiple therapeutic components may be a source of confusion and frustration to users. Individual components lack indicia signifying use of the Components together and components may be lost, misplaced, or ignored. Instructions issued separate from medication, as by the physician, may be lost. Furthermore, in spite of careful oral and written instructions from the health care provider, many patients are known to use what they have conviently available. Haphazard applications of medication can result in treatment failure and in the requirement for additional medical attention and cost.

Cost factors and outcomes are being carefully considered in the current medical climate. Improvements in organization and teaching including devices and methods which would facilitate treatments are considered desirable in view of limitations in time and costs for medical personnel. Successful therapy is less costly than unsuccessful treatment which eventuates in complications, multiple clinic visits, or hospitalizations.

In view of the aforementioned considerations, it is the object of the present invention to facilitate treatments which utilize topical aerosolized and oral medication together for treating diabetes mellitus in a human in order to make such regimens more convenient, encourage compliance and minimize error. The present invention teaches a unifying dispensing container for organizing and instructing diabetes mellitus treatment regimens which combine oral and aerosol medications and a method for enhancing the convenience and organization of such combined treatments. The unifying container incorporates a topical insulin preparation and at least one oral hypoglycemic agent, indicia for distinguishing these medications, and instructions for their coordinated use together as a single therapeutic regimen. It is to be understood that multiple doses of insulin and multiple doses of oral hypoglycemic agent are contained. The oral hypoglycemic medication may be in the form of tablet, pill, capsule, caplet, packets or containers of liquids, gels, or solids, some of which may require reconstituting, or any generally recognized oral form of medication. The topical insulin preparation may be in powder or liquid form suitable for aerosolization. The dispensing container may contain an aerosolizing device to deliver the insulin, and the insulin may preferably be incorporated therein.

SUMMARY OF THE INVENTION

A dispensing container which incorporates an aerosolizable topical insulin preparation, at least one oral hypoglycemic agent, and indicia and instructions for their coordinated use as a single therapeutic regimen for the treatment of diabetes mellitus. Also a method for treating diabetes mellitus in a human which employs such a device.

BRIEF DESCRIPTION OF THE DRAWINGS

FIG. 2 is plan view of another embodiment in accordance with the present invention.

DETAILED DESCRIPTION OF THE PREFERRED EMBODIMENT

Figure 1:
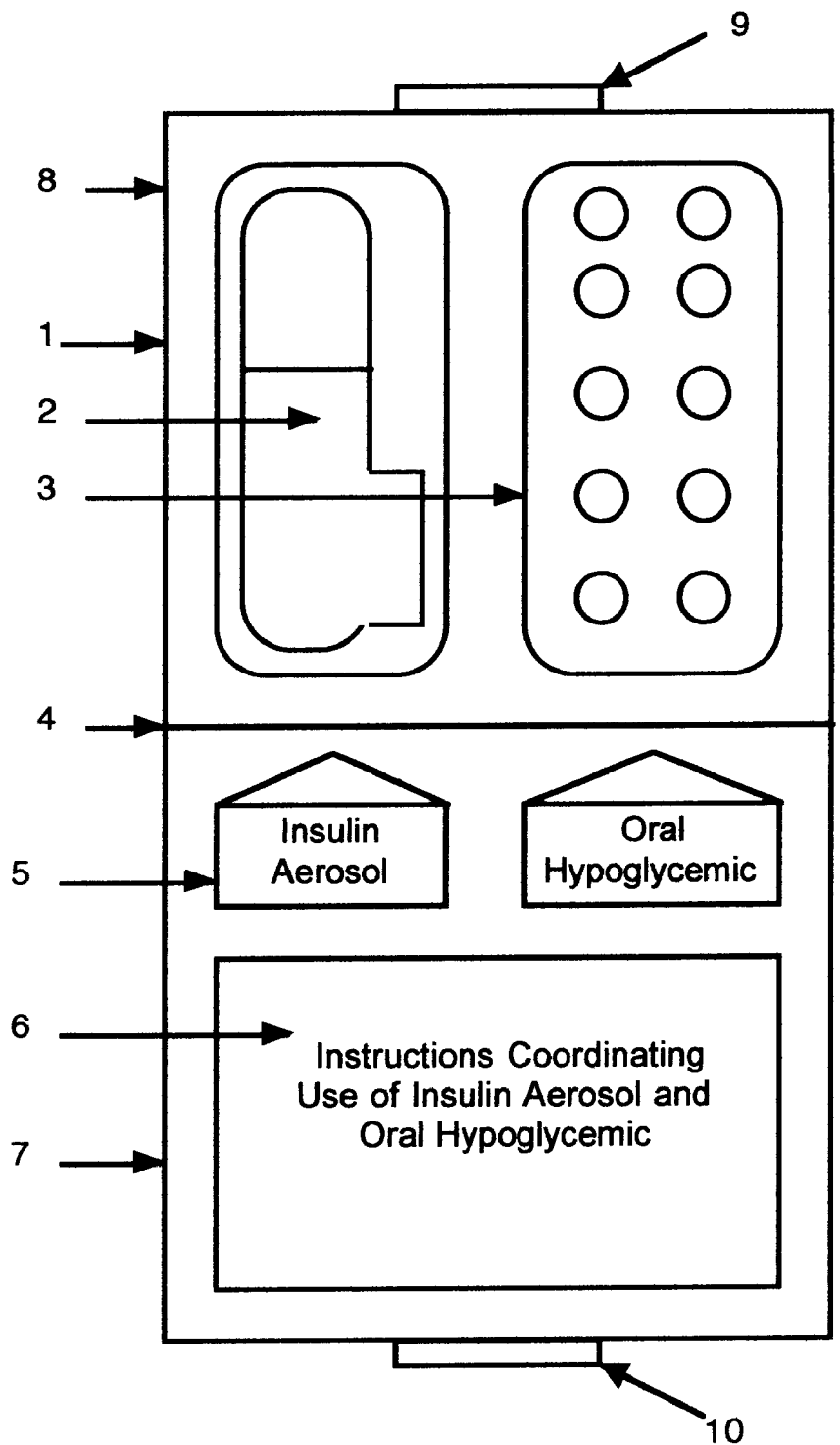
FIG. 1 is a plan view of an embodiment in accordance with the present invention

The following detailed description of the invention is provided to aid those skilled in the art in practicing the present invention. However, it should not be construed to unduly limit the present invention. Variations and modifications in the disclosed embodiments may be made by those of ordinary skill in the art without departing from the scope of the present inventive discovery.

Two embodiments of the unifying container of the preferred invention are depicted in FIG. 1 and FIG. 2. Referring to FIG. 1, a support package 1 which houses an insulin aerosol 2 and oral hypoglycemic agent in the form of tablets in a blister wrap 3 is illustrated. Techniques for making and attaching such wraps is well known and will not therefore be further described. A fold 4 in the package is provided in the center. Identifying indicia 5 is provided with respect to said topical insulin and oral hypoglycemic medication. An instruction bearing portion 6 provides instructions coordinating use of the topical and oral medication. The instructions are either unalterable or capable of being altered, yet maintained within the unifying container. FIG. 2 shows a frame 11 to accommodate interchangeable instructions. The instruction bearing portion may also include an erasable pad or a pad with multiple tear off sheets. The lid portion 7 and the bottom portion 8 of the support package each contain respective clasp portions 9 and 10 which can be secured together when the support package is folded along fold 4. FIG. 2 depicts an embodiment which contains a reservoir enclosing multiple doses of insulin 12, an aerosolizing device 13, and multiple doses of oral hypoglycemic medication in a capped bottle 14. It is to be understood that the reservoir enclosing multiple doses of insulin might consist of a vial, bottle, canister, or other container suitable for containing insulin. It is to be further understood that the device for aerosolizing said insulin might be of the venturi, ultrasonic, or other types known to be used for delivery of medical aerosols and modifications thereof to accomodate therapeutic insulin aerosolization. The instructions, in this instance, include instructions for transferring insulin from the reservoir 12 to the aerosolization device 13 and utilizing the aerosolization device 13 to dose insulin. FIG. 2 also depicts an optional thermal material 15, such as styrofoam or other insulating material, for the purpose of maintaining temperature in the area surrounding the insulin reservoir.

Although the embodiments specifically described herein have one aerosolized preparation and one oral medicament housing, packaging containing other numbers of aerosol and oral agent housings are also within the scope of this invention. The packaging may be adapted by widening the packaging and increasing the number of housings and indicia. Additionally, the packaging may be in any geometric configuration, particularly as needed to incorporate aerosolizing devices as may be desired.

The invention will be further clarified by a consideration of the following examples, which are intended to be exemplary of the invention. One treatment regimen utilizing topical inhaled insulin aerosol and oral hypoglycemic medication for the treatment of diabetes mellitus might include 100 U of aerosolized insulin administered by metered dose inhaler three time a day at the time of each main meal, and the oral hypoglycemic agent acarbose, one 50 mg tablet three times per day at the start of each main meal. Another regimen might include 100 U of aerosolized insulin administered in a nebulizer device three times a day at the time of each main meal and the oral hypoglycemic agent metformin hydrochloride, one 850 mg tablet three times a day at the times of each main meal. Regimens may be devised to include a combination of differing oral agents.

Other variations may occur to those skilled in the art which are within the scope of the invention as set forth in the appended claims. Those of skill in the art may also recognize modifications to these presently disclosed embodiments. These variations and modifications are meant to be covered by the spirit and scope of the present claims.

What is claimed is:

1. A diabetes mellitus treatment device comprising:

a dispenser for housing multiple dosages of aerosolizable insulin;

multiple dosages of at least one oral hypoglycemic medication;

indicia operably associated with said dispenser for distinguishing said multiple dosages of said aerosolizable insulin and said multiple dosages of said at least one oral hypoglycemic medication; and instructions operably associated with said dispenser for coordinating administration of said multiple dosages of said aerosolizable insulin and said multiple dosages of said at least one oral hypoglycemic medication as a regimen.

2. The device of claim 1 wherein said multiple dosages of said at least one oral hygoglycemic medication is in the form of a tablet, pill, capsule, caplet, liquid, powder or gel.

3. The device of claim 1 wherein said instructions can be altered yet maintained within the unifying container.

4. The device of claim 1 further comprising an aerosol device.

5. The device of claim 4 wherein said multiple dosages of said aerosolizable insulin is contained within said aerosol device.

6. The device of claim 1 further comprising insulating material disposed about said multiple dosages of said aerosolizable insulin.

7. A diabetes mellitus treatment device comprising:

a dispenser housing (a) multiple dosages of aerosolizable insulin;

(b) multiple dosages of at least one oral medication selected from the group consisting of sulfonylureas, biguanides, alpha-glucosidase inhibitors, and thiazolidinediones;

(c) indicia operably associated with said dispenser for distinguishing said multiple dosages of said aerosolizable insulin and said multiple dosages of said at least one oral medication; and (d) instructions operably associated with said dispenser for coordinating administration of said multiple dosages of said aerosolizable insulin and said multiple dosages of said at least one oral medication as a regimen.

8. The device of claim 7 wherein said multiple dosages of said at least one oral medication is in the form of a tablet, pill, capsule, caplet, liquid, powder or gel.

9. The device of claim 7 wherein said instruction can be altered yet maintained within the unifying container.

10. The device of claim 7 further comprising an aerosol device.

11. The device of claim 10 wherein said multiple dosages of aerosolizable insulin is contained within said aerosol device.

12. The device of claim 7 further comprising insulating material disposed about said multiple dosages of said aerosolizable insulin.

13. A method for treating diabetes mellitus in a human, said method comprising the steps of:

(a) providing a dispenser which contains multiple dosages of aerosolizable insulin, multiple dosages of at least one oral hypoglycemic medication, indicia for distinguishing said multiple dosages of said aerosolizable insulin and said multiple dosages of said at least one oral hypoglycemic medication, and instructions for coordinating administration of said multiple dosages of said aerosolizable insulin and said multiple dosages of said at least one oral hypoglycemic medication as a regimen; and (b) administering said multiple dosages of said aerosolizable insulin and said multiple dosages of said at least one oral hypoglycemic medication according to said indicia and said instructions.

14. A method for treating diabetes mellitus in a human, said method comprising the steps of:

(a) providing a dispenser which contains multiple dosages of aerosolizable insulin, multiple dosages of at least one oral medication selected from the group consisting of sulfonylureas, biguanides, alpha-glucosidase inhibitors, and thiazolidinediones, indicia for distinguishing said multiple dosages of said aerosolizable insulin and said multiple dosages of said at least one oral medication, and instructions for coordinating administration of said multiple dosages of said aerosolizable insulin and said multiple dosages of said at least one oral medication as a regimen; and (b) administering said multiple dosages of said aerosolizable insulin and said multiple dosages of said at least one oral medication according to said indicia and said instructions.

15. The treatment device of claim 1 wherein said at least one oral medication is selected from the group consisting of sulfonylureas, biguanides, alpha-glucosidase inhibitors, and thiazolidinediones.

* * * * *